United States Patent [19]
Aldrich et al.

[11] Patent Number: 5,279,791
[45] Date of Patent: Jan. 18, 1994

[54] LIQUID CONTROL SYSTEM FOR DIAGNOSTIC CARTRIDGES USED IN ANALYTICAL INSTRUMENTS

[75] Inventors: William Aldrich, Redwood City, Calif.; Daniel Gratiot, Watertown, Mass.

[73] Assignee: Biotrack, Inc., Mountain View, Calif.

[21] Appl. No.: 6,664

[22] Filed: Jan. 19, 1993

Related U.S. Application Data

[63] Continuation of Ser. No. 664,031, Mar. 4, 1991, abandoned.

[51] Int. Cl.⁵ .................... G01N 21/01; B01L 11/00
[52] U.S. Cl. .................................... 422/58; 422/99; 422/100; 422/102
[58] Field of Search ............... 422/58, 99, 100, 102

[56] References Cited

U.S. PATENT DOCUMENTS

| | | | |
|---|---|---|---|
| 3,913,790 | 10/1975 | Seidel | 422/100 X |
| 4,378,895 | 4/1983 | Woinarski | 220/306 |
| 4,550,024 | 10/1985 | le Granse | 426/77 |
| 4,756,884 | 7/1988 | Hillman et al. | 422/81 X |
| 4,868,129 | 9/1989 | Gibbons et al. | 422/100 X |
| 4,946,795 | 8/1990 | Gibbons et al. | 422/100 X |
| 4,952,373 | 8/1990 | Sugarman et al. | 422/61 X |

*Primary Examiner*—James C. Housel
*Assistant Examiner*—Arlen Soderquist
*Attorney, Agent, or Firm*—Cooley Godward Castro Huddleson & Tatum

[57] ABSTRACT

A liquid control system for a diagnostic cartridge that is insertable into an analytical instrument, which has a liquid control region located at a border between interior and exterior surfaces of the cartridge when the cartridge is inserted into a slot in the analytical instrument, wherein the region is adapted to fit with an edge formed by exterior surfaces of the analytical instrument and the slot, thereby providing a capillary gap at the edge having a gap width smaller than any gap width of any space contiguous to the gap in the interior of the slot when the cartridge is inserted in the instrument.

7 Claims, 3 Drawing Sheets

5,279,791

LIQUID CONTROL SYSTEM FOR DIAGNOSTIC CARTRIDGES USED IN ANALYTICAL INSTRUMENTS

CROSS REFERENCE TO RELATED APPLICATIONS

This application is a continuation of U.S. application Ser. No. 07/664,031, filed Mar. 4, 1991 now abandoned.

BACKGROUND OF THE INVENTION

1. Technical Field

This invention relates to diagnostic devices for analyzing blood and other liquids in analytical instruments and more particularly to shields for such devices intended to confine the excess liquid to the diagnostic device and to prevent contamination of the instrument.

2. Background

U.S. Pat. Nos. 4,868,129 and 4,946,795 and U.S. application Ser. No. 117,791, filed Nov. 5, 1987, now U.S. Pat. No. 5,077,017 issued Dec. 31, 1991, disclose disposable diagnostic devices in the form of a cartridge which, with the use of a monitor, can be used to automatically dilute a sample of blood and determine the analytical values of various components of blood. Such instantaneous determination of such tests is of great value both to patients and to physicians in that it permits prompt diagnosis of a disease state, prescription of appropriate medication, and monitoring of the proper dosage of medication. While the present invention has broad applications beyond these specific examples, they will be used throughout this application as typical applications.

Each of these devices mentioned above is roughly two-thirds the size of a conventional audio cassette tape and is a single use disposable item. They are used with suitable monitors about the size of a medium-sized audio cassette player that have a receiving slot therein into which the cartridge is partially inserted in preparation for the measurement. Each cartridge has a liquid receiving area which remains outside the monitor and into which the liquid to be analyzed is deposited, such as blood added directly from a pricked finger or by using a capillary tube, syringe, or the like.

Two related problems and disadvantages have been recognized, and the present invention has been developed to solve both of them. Both problems are related to the occasional, inadvertent seepage of excess or misapplied liquid from the surface of the cartridge into the interior of the monitor. This seepage can be caused by gravity flow, but it is often assisted by capillarity, as the cartridge closely fits into its receiving slot and forms numerous spaces of capillary dimensions around its perimeter.

In severe cases, seepage can occur so that the diagnostic system within the monitor will not operate properly. Specifically, internal sensors present in the monitors for the cartridges described above, such as light sensing transducers and other instruments, can be affected by the unintentional presence of liquid, such as blood. If, when the self-diagnostic check is being run, the readings from the sensors are outside of the expected ranges, the monitor will withhold the reporting of any test results until the readings return to the normal range, which cannot happen with contaminated instruments until the instrument is cleaned.

A related problem, apart from having liquid interfere with the operation of the monitor, is the contamination of the monitor which results from contact of a biological test liquid, such as blood, with either the interior or exterior of the monitor. Not only is such contact unsightly and unsanitary, but the hazards of cross-contamination of cartridges with potentially infected bodily liquids of the test subject and the desirability of preventing such contact are so apparent as to require no detailed elaboration. Although surface spills cannot always be avoided and must be cleaned up by the user with care being given to possible infectivity, spills that reach the interior of a monitor can cross-contaminate other cartridges without being recognized by the user. Thus, systems that protect the interior of the monitor from contamination are highly desirable.

A number of these problems have been solved in the laboratories of the present inventors for a different type of cartridge described in U.S. Pat. No. 4,756,884. This cartridge is similar in that it also fits into a monitor and has a liquid receiving area which remains outside the monitor and onto which blood is deposited for analysis. However, this earlier device is not intended for dilution and is therefore smaller than and of a different shape from the devices for which the present invention was developed. The former cartridge was relatively flat, with a broad upper surface. The newer cartridges are tall and narrow. Accordingly, the problem of blood contamination of the monitor using the earlier cartridges, which is described in U.S. Pat. application Ser. No. 341,757, filed Apr. 21, 1989, now U.S. Pat. No. 4,952,373, issued Aug. 28, 1990, was solved in a manner that cannot be directly applied to the present situation. This solution involved a blood shield which comprised a resilient member which, in its free state, projects away from the surface of the device to a distance sufficient to assure that it covers any gap between the liquid receiving surface of the device and the monitor in order to confine excess liquid to the surface of the device and prevent it from entering the monitor. The shield was generally provided with sufficient resiliency to permit it to lie flat with the cartridge in its packaged state, but to automatically project upward when the package was opened so that the device is ready for use.

However, this type of shield is not appropriate for all types of devices, particularly devices in which contamination is likely to occur on more than one surface of the inserted cartridge. In such cases, particularly when the cartridge is designed to be inserted into a top or side surface of the monitor, contamination could occur at the corners of such device, where it would not be possible to provide protection with the flexible, pop-up shield as described. Accordingly, there remains a need for further development in shielding the interior of analytical instruments (monitors) from contamination by blood or other liquids misapplied to a cartridge inserted in the monitor.

SUMMARY OF THE INVENTION

The present invention provides a liquid control region for a diagnostic cartridge that is insertable into an analytical instrument, which comprises a liquid control region located at a border between interior and exterior surfaces of the cartridge when the cartridge is inserted into a slot in the analytical instrument, wherein the region is adapted to closely fit with an edge formed by exterior surfaces of the analytical instrument and the slot, thereby providing a capillary gap at the edge smaller than any space in the interior of the slot that is contiguous to the capillary gap when the cartridge is inserted in the instrument. The present invention relies on the creation of a capillary space that will retain any spilled liquid in an easily cleaned region on the exterior surface of the instrument. This contrasts with prior physical barriers, which attempted to prevent the liquid being analyzed from reaching any existing capillary space surrounding the cartridge when a spill took place.

BRIEF DESCRIPTION OF THE FIGURES

This invention will be better understood by reference to the following detailed description of specific embodiments when considered in combination with the drawings that form part of this specification, wherein.

DETAILED DESCRIPTION OF SPECIFIC EMBODIMENTS

Figure 1:
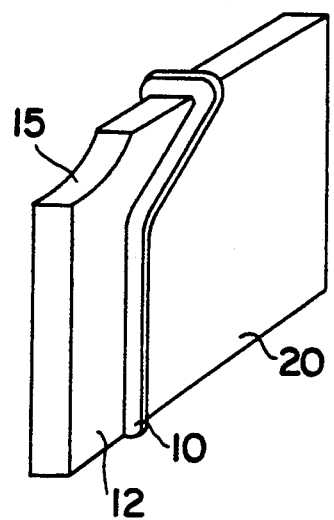
FIG. 1 is a perspective view of a liquid diagnostic cartridge with a liquid control region according to the present invention.

The present invention provides a liquid control region particularly suited for use with liquid diagnostic devices which receive liquid at one surface and are used in connection with other equipment, such as an electronic monitor into which the liquid might be accidently spilled. The device of the present invention, in contrast to prior devices which have attempted to prevent capillarity from coming into play, uses capillarity created at the edge of the monitor by insertion of the cartridge; previously such capillarity had caused problems by drawing spilled liquid into the interior of the monitor. However, when the control region of the present invention is designed and used as described herein, the newly designed capillary region causes liquid to be retained at an outer surface of the analytical instrument even under spill conditions that would overwhelm previous liquid guards. This is accomplished by providing a liquid control region on a surface of the insertable cartridge which closely approaches a matched region at the edge of the slot into which the analytical cartridge is being inserted. By closely matching these surfaces, a small capillary gap is provided around the edge of the slot where protection against contamination is desired. Although other capillary spaces can exist inside the slot when the cartridge is inserted, the slot is designed so that any spaces that are contiguous to the capillary gap and in the interior of the slot are bigger than the capillary gap. Since capillary forces tend to draw liquids into smaller spaces and further prevent (or at least hinder) liquids from entering a larger space from a smaller capillary space, capillary forces act to retain to spilled liquid at the edge of the slot rather than drawing it into the slot itself. Accordingly, contamination of the difficult-to-clean interior of the slot is avoided.

The specific shape of the liquid control region is not material to the practice of the present invention. In one preferred embodiment that is discussed in detail below, the control region projects outward from the surface of the cartridge. However, this form of the control region was selected solely for convenience, since the control cartridge and analytical instrument to which this invention was first applied had already been designed and since the intent was to slide the analytical cartridge into an open slot in the analytical instrument. In a system that retains its analytical cartridge by a different system, other physical shapes can exist. Several examples presented at the end of the following detailed discussion of the preferred embodiment of the invention illustrate some of the many variations that can exist.

In a similar manner, the length of the protected region will vary with the geometry of the particular cartridge and monitor being protected. For example, the edge of the slot at the bottom of the cartridge does not normally need to be protected, since the cartridge itself protects the bottom edge from spills, unless the geometry of the cartridge or monitor is such that spills can be channelled to the bottom of the cartridge. Here "bottom" refers to the normal operating orientation of the cartridge/monitor combination above which some portion of the cartridge normally resides. Similarly, some perimeter regions can be protected by other means, such as the methods described in the background section of this specification. In preferred embodiments, additional flow directors, such as channels or ridges in the exterior surface of the cartridge, can be used to direct excess liquid away from the capillary gap at the control region.

A continuous control region around the entire cartridge is not necessary, but can be used if desired. A useful guiding principle that can be used to design cartridges with control regions is to prepare a cartridge/monitor combination without a control region and apply liquid in all possible inappropriate manners while monitoring liquid flow. Any region reached by liquid can be protected by the control region of the invention. Preferred edges those where any upper surface of the monitor meets the inserted cartridge as well as any to which flow of liquid can occur from an upper surface of the monitor or cartridge. An upper surface is one on which a liquid drop can fall vertically when the cartridge in inserted in the monitor and both are in their normal operating position. A continuous barrier at all such edges is most preferred.

Turning now to the drawings in which the same reference numbers refer to functionally equivalent features throughout, FIG. 1 is a perspective drawing showing liquid control region 10 in the form of a ridge extending outward from the surface of analytical cartridge 20. Additional ridges 12 are present on the exterior surface of the cartridge to direct spilled sample away from the monitor even before it reaches the control region in this preferred embodiment. Sample application site 15 is visible on an outer surface of cartridge 20. As will be evident from later figures, the surfaces of cartridge 20 to the right of ridge 10 will be in the interior of the monitor slot while the cartridge is being used, while surface to the left of ridge 10 will be exterior to the monitor.

Figure 2:
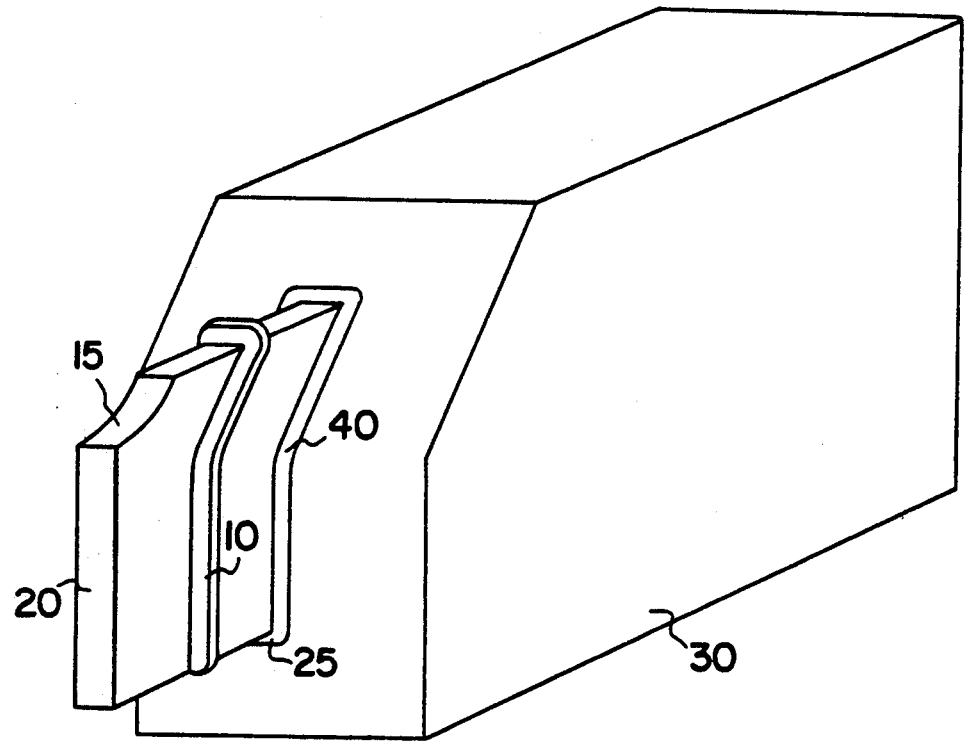
FIG. 2 is a perspective view of the cartridge and liquid control region of FIG. 1 being partially inserted into a monitor.

FIG. 2 shows cartridge 20 partially inserted into cartridge slot 25 of analytical instrument (monitor) 30. Depression 40 is visible around the edge of the slot. When cartridge 20 is fully inserted into slot 25 by pushing on cartridge 20 in the direction of the arrow shown in FIG. 2, liquid control region (ridge) 10 closely fits into depression 40. There are no particular requirements on the shape of the depression. It is desirable to have the outer face of the ridge form a planar surface with the outer face of the monitor. However, this is not required. The depression simply functions in combination with the ridge or other formed control region to provide the desired capillary gap and (in preferred embodiments) to assist in forming the larger contiguous space and to provide a separate surface that traps the excess liquid after the cartridge is removed so that it can easily be cleaned.

Figure 3:
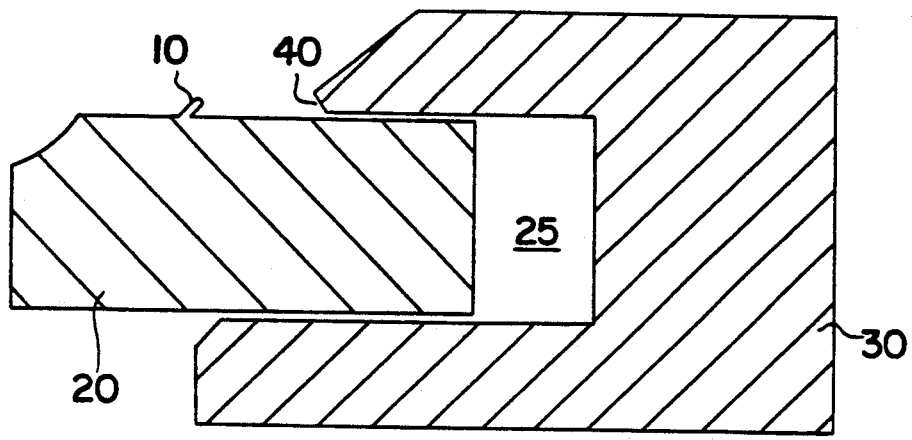
FIG. 3 is a vertical cross-sectional view of the cartridge, liquid control region, and monitor of FIG. 2.

A vertical cross-sectional view of the embodiment shown in FIG. 2 is shown in FIG. 3. Again, cartridge 20 is partially inserted into slot 25 of analytical instrument 30. At the time illustrated, cartridge 20 has not been pushed sufficiently into slot 25 to engage liquid control ridges 10 in depression 40 at the edge of the slot. However, the potential for a close fit at the edges is evident from this figure.

Figure 4:
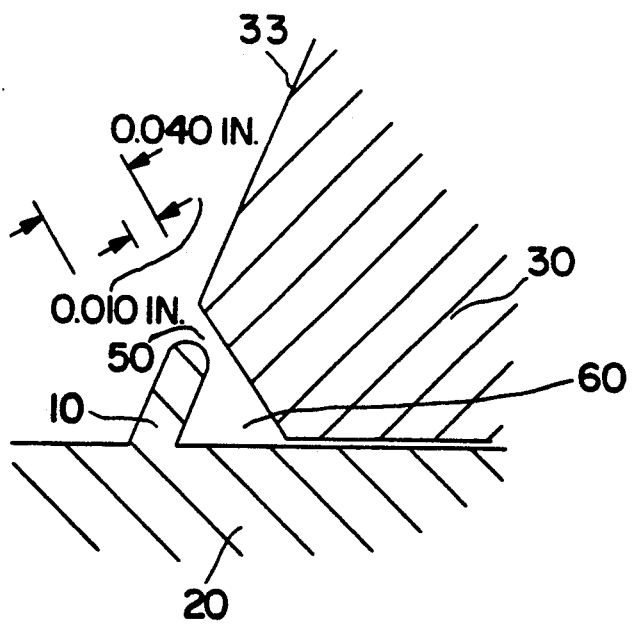
FIG. 4 is a partial vertical cross-sectional view of the liquid control region of the cartridge and monitor of FIG. 2 fully inserted into the monitor.

FIG. 4 shows in detail the close fit that occurs at depression 40 when the cartridge is fully inserted into the slot. FIG. 4 shows only the detail of the fit at edge 40 without showing the remainder of cartridge 20 or monitor 30. An additional feature of this preferred embodiment is that the outer surface of ridge 10 and outer surface 33 of monitor 30 together form a planar surface to help direct spills past the capillary gap (by gravity-directed liquid flow).

As can be seen in the figure, capillary gap 50 is created which has a gap dimension smaller than the gap dimension in region 60 which is contiguous to the capillary gap. As an example, the capillary gap at the edge in one embodiment was 0.010 inch (0.25 mm) as shown for gap 50 with the contiguous interior space 60 having a gap dimension of 0.040 inch (1.0 mm). In preferred embodiments space 60 contiguous to the capillary gap is itself non-capillary, so that even large spills of liquid onto the outer surface of cartridge 20 will be blocked from entry into space 60. However, space 60 can be of sufficiently small dimensions so that liquid would have been drawn into slot 25 in the absence of control region 10 and capillary gap 50. In such cases the presence of capillary gap 50 tends to cause spilled liquids to be retained in the capillary gap and flow around the edge of the capillary gap preferentially to entering space 60. Such a design is quite satisfactory for cartridges and monitors in which the cartridge enters the monitor on a vertical (or nearly vertical) face of the monitor, as shown in FIG. 1–4. In such cases blood or other spilled liquids will be drawn around the edge of the gap and tend to flow off the lowest part of the capillary gap onto the adjoining outer surface of the monitor. However, when the cartridge enters an entirely horizontal, upper surface of a monitor so that flow away from the edge does not readily occur, contiguous interior spaces that are non-capillary are preferred for greater safety.

Capillary gaps and other capillary regions will generally have at least one dimension perpendicular to the flowpath in the range 0.01 to 2.0 mm, more generally 0.1 to 1.0 mm. A region is a capillary channel if both dimensions at right angles to the direction of flow are in the range required to support flow. A region is a capillary chamber if one dimension at right angle to flow is not in the range to support capillary flow; capillary flow is still maintained by having the second dimension at right angles to flow in the required range (similar to the space between two flat plates that are closely spaced). The capillary gap is generally an extended region of the perimeter of slot 25 and is thus a very short capillary chamber, thus giving rise to the phrase capillary gap.

It will be recognized that the actual size necessary to support capillary flow will vary with the liquid, the nature of the surface contacted by the liquid, and the contact angle between the liquid and the surface. Accordingly, the numerical values identified above are generally valid for aqueous liquids and plastic surfaces, but the actual gaps necessary to achieve capillary flow for a particular liquid/surface-material pair should be verified empirically. Significant variation from the numerical values can occur, but the principle of a capillary gap at the edge between the interior and exterior of the cartridge with a larger contiguous interior space still applies.

Figure 5:
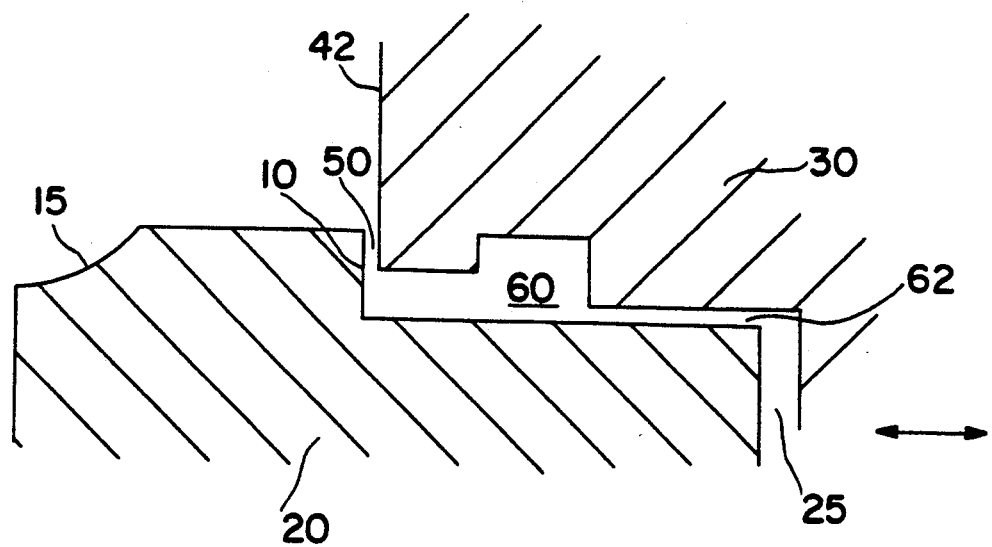
FIG. 5 is a partial cross-sectional view of an alternative embodiment of a cartridge and monitor of the invention.
Figure 6:
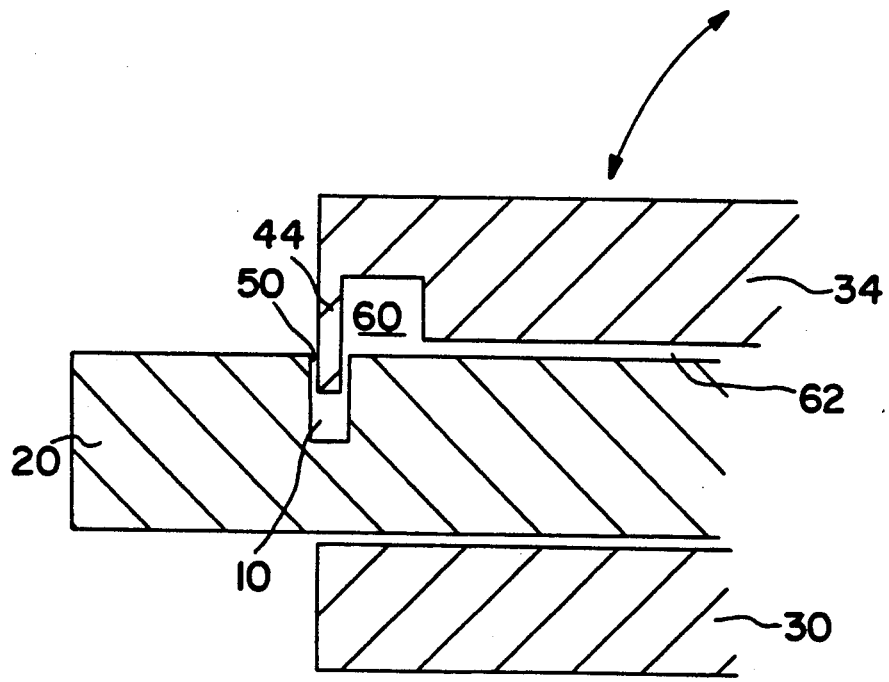
FIG. 6 is a partial cross-sectional view of a third embodiment of a cartridge and monitor of the invention.

A variety of different liquid control regions are shown in FIGS. 5 and 6. In each of these figures, only an area of the cartridge and monitor in the region of the capillary gap formed at the edge of the slot is shown.

FIG. 5 is a cross-sectional view of an embodiment in which cartridge 20 moves in slot 25 of monitor 30 in a direction shown by the double-headed arrow. Cartridge 20 is inserted into the slot by moving it in the direction to the right as shown in the figure and removed from the slot by moving it to the left. In this embodiment, there is no depression at the edge of the slot. Rather, control region 10 is the wall formed when the thickness of cartridge 20 varies at the edge of the gap. Capillary gap 50 forms when this wall 10 closely approaches outer surface 42 of monitor 30. Space 60, which is in the interior of slot of 25 and contiguous to capillary gap 50, is specifically designed to provide a non-capillary space, thereby assisting in the retention of excess sample in capillary gap 50. Interior walls of slot 25 can closely approach cartridge 20 in regions that are not contiguous to the capillary gap 50, such as shown when capillary gap 62 is formed in the interior of slot 25. However, since sample does not reach this region, no capillary forces act to draw sample into the interior of slot 25.

FIG. 6 shows an embodiment in which the liquid control region 10 is a depression in the surface of cartridge 20. In the partial vertical cross-section shown in FIG. 6, monitor 30 is designed with a hinged top section 34 (much in the manner of a waffle iron) which is raised and lowered for insertion and removal of cartridge 20 as shown by the arrow. A ridge 44 at the edge of slot 25 fits into depression 10 to form capillary gap 50. Space 60 prevents entry of sample into interior capillary space 62.

It will be recognized by one skilled in the art that these embodiments are merely representative of numerous embodiments that can provide a capillary gap at the edge of the slot into which an analytical cartridge is inserted. Certain advantages exist for particular embodiments. For example, the embodiments shown in FIGS. 4 and 5 allow unidirectional motion for cartridge insertion and removal and simplify design of the monitor. FIG. 6 allows access to the interior of the monitor for maintenance or other functions. Selection of a particular design can readily be made based on the needs of a particular cartridge and monitor.

The operation of the liquid control region is considered to be apparent from the foregoing discussion. Briefly explaining it with specific reference to FIG. 5, however, liquid may be added to the well 15 of the cartridge 20 directly from a pricked finger, or using any other conventional means, such as a capillary tube or syringe. Under normal circumstances a single drop or two of the liquid is sufficient for the analysis and will be readily contained in the well. Under these condition, the liquid control region 10 will be unnecessary to block liquid, although it may still fulfill other useful functions, such as light blocking. In the event excess liquid is introduced onto the surface of the cartridge, the possibility exists that, without the liquid control region of the present invention, the liquid might reach the interior of slot 25 and/or enter gap 62. It must be recognized that the embodiment of the liquid control region shown in the figures may not be effective against a "flood" of a great excess of liquid. It will, nevertheless, be effective in the vast majority of instances where there is a moderate excess of liquid, or where an otherwise proper amount of liquid is errantly applied.

From the above discussion, it will be appreciated that there is described a liquid control region for use with diagnostic cartridges which can be applied to cartridges of existing design without necessitating any changes to the basic cartridge manufacture or to the design or manufacture of the monitor designed for use with the cartridges.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A liquid control system for preventing fluid from entering within an analytical instrument, wherein said system comprises: in combination
    a diagnostic cartridge that accepts liquid samples;
    an analytical instrument having a slot for insertion of a portion of said diagnostic cartridge within said analytical instrument;
    a ridge projecting outward from at least one face of said diagnostic cartridge; and
    a first surface located at an edge formed by exterior surfaces of said analytical instrument and interior surfaces of said slot wherein first and second gaps are formed when said diagnostic cartridge is inserted in said slot, said first gap being formed between said ridge and said first surface and having a capillary gap width, said second gap being formed contiguous to said first gap within the analytical instrument between said diagnostic cartridge and said interior surfaces of said slot and having a gap width which is larger than any adjacent capillary gap width of said first gap, and wherein said first gap is absent in a region beneath said diagnostic cartridge to allow fluid collected in said first gap to drain.

2. The liquid control system of claim 1, wherein said first surface is formed as a depression at said edge of said slot.

3. The liquid control system of claim 2, wherein said ridge has an interior portion facing said depression and an exterior portion facing away from said depression so that an exterior surface of said instrument and said exterior portion of said ridge together form a planar surface.

4. The liquid control system of claim 1, wherein said ridge continuously projects outward from all surfaces of the diagnostic cartridge adjacent to said edge except a bottom surface.

5. The liquid control system of claim 1, wherein said second gap has a non-capillary gap width.

6. A liquid control system for preventing fluid from entering within an analytical instrument, wherein said system comprises: in combination
    a diagnostic cartridge that accepts liquid samples;
    an analytical instrument having a slot for insertion of a portion of said diagnostic cartridge within said analytical instrument;
    a depression in at least one face of said diagnostic cartridge; and
    a first surface located at an edge formed by exterior surfaces of said analytical instrument and interior surfaces of said slot wherein first and second gaps are formed when said diagnostic cartridge is inserted in said slot, said first gap being formed between said depression and said first surface and having a capillary gap width, said second gap being formed contiguous to said first gap within the analytical instrument between said diagnostic cartridge and said interior surfaces of said slot and having a gap width which is larger than any adjacent capillary gap width of said first gap, and wherein said first gap is absent in a region beneath said diagnostic cartridge to allow fluid collected in said first gap to drain.

7. The liquid control system of claim 6, wherein said second gap has a non-capillary gap width.

* * * * *